United States Patent [19]

Hyatt

[11] 4,294,761

[45] Oct. 13, 1981

[54] PREPARATION OF 7,12-DIOXASPIRO[5,6]DODECANE-3-ONE

[75] Inventor: John A. Hyatt, Kingsport, Tenn.

[73] Assignee: Eastman Kodak Company, Rochester, N.Y.

[21] Appl. No.: 121,549

[22] Filed: Feb. 14, 1980

[51] Int. Cl.³ .......................................... C07D 321/10
[52] U.S. Cl. ....................................................... 260/338
[58] Field of Search ........................................ 260/338

[56] References Cited

FOREIGN PATENT DOCUMENTS 2005266 4/1979 United Kingdom .

OTHER PUBLICATIONS

Courtot, Bull. Soc. Chim. France (1962), pp. 1493–1494.
Lednicer et al., J. Med. Chem., vol. 22(10), pp. 1157–1158, (1979).

Primary Examiner—Henry R. Jiles
Assistant Examiner—Bernard Dentz
Attorney, Agent, or Firm—J. Frederick Thomsen; Daniel B. Reece, III

[57] ABSTRACT

Disclosed is the title compound and its preparation by the reaction of 1,4-cyclohexanedione and 1,4-butanediol. The title compound is useful as a pharmaceutical intermediate.

1 Claim, No Drawings

PREPARATION OF 7,12-DIOXASPIRO[5,6]DODECANE-3-ONE

This invention pertains to the mono-ketal from 1,4-butanediol and 1,4-cyclohexanedione and the process by which it is prepared.

The use of 1,4-cyclohexanedione as an intermediate in organic synthesis requires modification or "protection" of one of the dione keto groups so as to leave only one keto function available for reaction. This has previously been accomplished by forming the mono-ketal from 1,4-cyclohexanedione and ethylene glycol (P. Courtat, *Bull. Soc. Chim. Fr.* 1962, 1493; J. Lambert, *J.A.C.S.* 89, 1836 (1967). The preparation of this mono-ketal is handicapped by modest yield and serious isolation problems requiring chromatographic or complicated extraction procedures. These yield and isolation problems are due primarily to the formation of significant amounts of bis(ketal) in the reaction of 1,4-cyclohexanedione and ethylene glycol. Similar results are obtained using 1,3-propanediol or neopentyl glycol.

I have discovered that 1,4-butanediol is unique in its behavior as the glycol component in the synthesis of a mono-ketal of 1,4-cyclohexanedione in that the product monoketal, 7,12-dioxaspiro[5,6]dodecane-3-one, which has the structure I, is formed in high yield and is accompanied by only small amounts of bis(ketal).

Compound I is equivalent as a synthetic intermediate to the previously described ethylene glycol monoketal of 1,4-cyclohexanedione, the utility of which has been pointed out in the literature (Courtat, ibid.; Lambert, ibid.; Haslanger and Lanton, Syn. Comm. 4(3), 155 (1974); Marshall and Flynn, *Syn. Comm.* 9(2), 123 (1979) Ledincer et al, J. Med. Chem. 22, 1157 (1979); U.K. Patent Application No. 2,005,266 (4-19-79)). In addition, Compound I can be used to prepare quinone methides such as II and phenols of the type III. These compounds are useful as pharmaceutical intermediates.

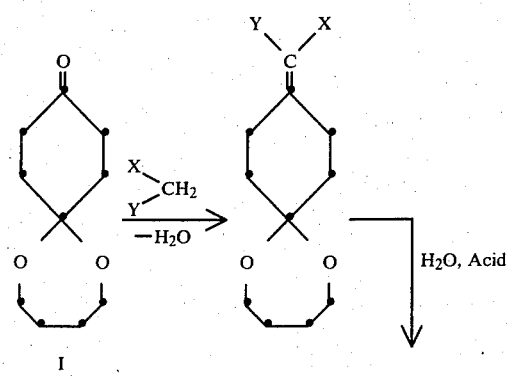

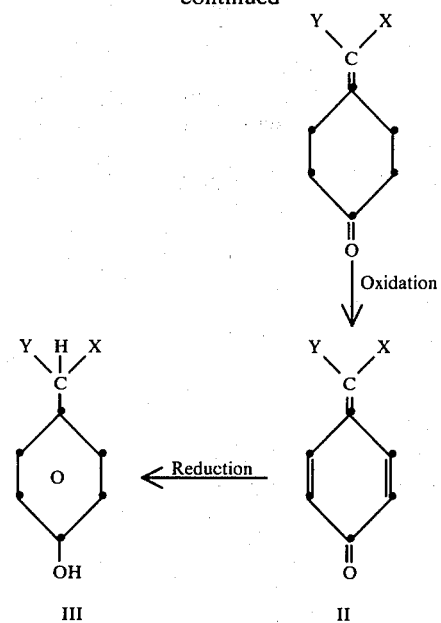

wherein X, Y are chosen from —CN, $CO_2R$, —$SO_2R$; R=$C_1$–$C_6$ alkyl, aryl, or substituted aryl.

My novel process thus comprises reacting under dehydrating conditions 1,4-butanediol and 1,4-cyclohexanedione in the presence of an inert hydrocarbon solvent in the presence of an effective amount of a ketal-forming, acid catalyst. Mono-ketal I is formed in a yield of about 80% with only about 15% of the bis-ketal being formed. I is isolable in pure form by simple fractional distillation.

The reaction conditions employed in the preparation of I are those conventionally used in the synthesis of ketals. Carrying out the process under dehydrating conditions requires that the water of reaction be removed during the process. This can be accomplished by azeotropic distillation or by the presence of dehydrating agents such as magnesium sulfate, calcium chloride, molecular sieves and the like. Azeotropic distillation is the more practical means of water removal and thus is preferred. It is apparent that the reactants should be essentially free of water.

The hydrocarbon solvents that can be used in the process include aromatic and saturated aliphatic hydrocarbons. The aromatic hydrocarbons such as benzene, toluene and the xylenes which form efficient azeotropes with water are preferred. The temperature range over which the process can be conducted can be varied substantially depending on the solvent and pressure employed. Generally, temperatures in the range of 50° to 150° C. can be used with temperatures of 70° to 110° C. being preferred. The acid catalyst can be selected from the mineral acids and the organic sulfonic acids including acidic ion-exchange resins such as Amberlyst 15. Examples of such acids include benzene-sulfonic acid, the toluenesulfonic acids, naphthalenesulfonic acid, sulfuric acid, phosphoric acid and hydrochloric acid. In view of the product that is desired, the molar ratio of the reactants used will be approximately 1:1.

My novel process is further illustrated by the following example.

EXAMPLE 1

A mixture of 56.0 g (0.5 mole) of 1,4-cyclohexanedione, 0.5 g of p-toluenesulfonic acid, and 500 ml of toluene was stirred at reflux under a Dean-Stark water separator. 1,4-Butanediol (45 g, 0.5 mole) was added dropwise over two hours, during which time 9.0 g (0.5 mole) water was removed from the reaction mixture. The reaction mixture was cooled, washed with aqueous sodium bicarbonate solution, and dried over $MgSO_4$. Gas chromatographic analysis of the resulting yellow solution showed the presence of 6.0% unreacted diol, 83% monoketal I, and 11% bisketal. Distillation in vacuo afforded pure 9, boiling point 108°–114° (2.7 mm Hg). IR (Neat): 5.85, 8.00, 8.90, 11.72 $\mu$. NMR ($CDCl_3$): $\delta$ 3.80 (m, 4H); 2.50 (t, 4H); 2.00 (t, 4H); 1.72 (m, 4H).

Analysis: Calc'd. for $C_{10}H_{16}O_3$: C, 65.19%, H, 8.76%. Found: C, 65.30; H, 8.91%. Mass Spectrum: m/e 184.

The invention has been described in detail with particular reference to certain preferred embodiments thereof, but it will be understood that variations and modifications can be effected within the spirit and scope of the invention.

I claim:

1. Process for the preparation of 7,12-dioxaspiro[5,6]-dodecane-3-one which comprises reacting under dehydrating conditions 1,4-cyclohexanedione and 1,4-butanediol in an inert hydrocarbon solvent in the presence of an effective amount of a ketal-forming, acid catalyst.

* * * * *